United States Patent
Fornara et al.

(10) Patent No.: US 8,455,011 B2
(45) Date of Patent: Jun. 4, 2013

(54) ADJUVANT COMPOSITIONS FOR HERBICIDES

(75) Inventors: Dario Fornara, Novara (IT); Cristina Picco, Nosate (IT); Giuseppe Li Bassi, Gavirate (IT)

(73) Assignee: Lamberti SpA, Albizzate (IT)

( * ) Notice: Subject to any disclaimer, the term of this patent is extended or adjusted under 35 U.S.C. 154(b) by 0 days.

(21) Appl. No.: 13/254,359

(22) PCT Filed: Feb. 19, 2010

(86) PCT No.: PCT/EP2010/052094
§ 371 (c)(1),
(2), (4) Date: Sep. 1, 2011

(87) PCT Pub. No.: WO2010/100039
PCT Pub. Date: Sep. 10, 2010

(65) Prior Publication Data
US 2011/0319265 A1    Dec. 29, 2011

(30) Foreign Application Priority Data
Mar. 3, 2009   (IT) .............................. VA2009A0017

(51) Int. Cl.
*A01N 25/00*   (2006.01)
*A01N 59/02*   (2006.01)
*A01N 33/04*   (2006.01)

(52) U.S. Cl.
USPC ........................................ 424/710; 504/116.1

(58) Field of Classification Search
None
See application file for complete search history.

(56) References Cited

U.S. PATENT DOCUMENTS

| | | | | |
|---|---|---|---|---|
| 5,356,861 A | * | 10/1994 | Gednalski et al. | 504/206 |
| 6,364,926 B1 | * | 4/2002 | Gryzik et al. | 71/64.1 |
| 6,645,914 B1 | * | 11/2003 | Woznica et al. | 504/206 |

FOREIGN PATENT DOCUMENTS

WO    WO-0069261    * 11/2000

* cited by examiner

*Primary Examiner* — Alton Pryor
(74) *Attorney, Agent, or Firm* — Mossman Kumar & Tyler PC

(57) ABSTRACT

Homogeneous aqueous composition containing from 10 to 350 g/Kg of ammonium sulfate and from 10 to 200 g/Kg of anionic esters of linear or branched C6-C20 alkyl polyglycosides, and diluted sprayable herbicidal formulation comprising the above homogeneous aqueous composition and from 0.01 to 5% by weight at least a herbicide.

15 Claims, No Drawings

ADJUVANT COMPOSITIONS FOR HERBICIDES

FIELD OF THE INVENTION

The present invention relates to homogeneous and stable aqueous concentrated adjuvant compositions containing ammonium sulfate and anionic esters of alkyl polyglycosides.

The invention additionally relates to stable sprayable diluted herbicidal formulations containing the above aqueous adjuvant compositions and at least a herbicide.

BACKGROUND OF THE ART

Many known agrochemicals have shown to be more effective in combination than when applied individually.

Herbicides, and in particular glyphosate, are usually sprayed in combination with organic adjuvants (such as surfactants acting as wetting agents and stickers) and inorganic adjuvants (such as inorganic nitrogen containing fertilizers). The presence of the various adjuvants guarantees good phytoactivity and avoids detrimental and/or unpredictable effects due to local conditions (water hardness, soil quality, weather conditions etc).

Among the several documents reporting combinations of adjuvants we cite:

U.S. Pat. No. 6,852,674, which describes a herbicidal mixture comprising a benzoyl derivative, a fertilizer containing nitrogen and an organic adjuvant;

U.S. Pat. No. 6,479,437, which describes a herbicidal mixture of a 3-heterocyclyl-substituted benzoyl derivative, a nitrogenous fertilizer and an organic adjuvant;

EP 058 4227, which reports a herbicidal composition comprising a effective amounts of a substituted cyclohexanedione, at least one nitrogen containing fertilizer that is present in an amount that increases the herbicidal activity of the substituted cyclohexanedione and one or more organic adjuvants;

EP 498 145, which reports glyphosate solid compositions comprising at most 10% of water, and discloses that the combination of an ammonium salt with alkyl polyglycosides enhances the phytoactivity of the glyphosate in a notably, nonexpected manner.

Unfortunately, inorganic nitrogen fertilizers are solid salts with limited solubility in water and herbicides may be poorly soluble in water. This is particularly the case for the combination of ammonium sulfate and glyphosate, which is well known to partially crystallize from its aqueous solution even when dosed for proper phytoactive application on the field in diluted form.

The addition of various surfactants to the aqueous ammonium sulfate solutions has been proposed to avoid crystallization and, eventually, to further increase the biological activity of the glyphosate.

US RE36,149 describes the preparation of a homogeneous and stable aqueous ammonium sulfate blend with a non ionic alkyl polyglycoside.

The amount of ammonium sulfate in the solution is reported to be about 8.5 pounds (3.145 Kg) for about 2.5 gallons (9.475 l) of the blend, corresponding to about 27% by weight of ammonium sulfate.

The blend is then mixed in locus with a solution of glyphosate and sprayed on the weeds.

SUMMARY OF THE INVENTION

We have now discovered that aqueous compositions containing up to 350 g/Kg, preferably from about 10 to about 350 g/Kg, of ammonium sulfate and from about 10 to about 200 g/Kg of anionic esters of alkyl polyglycosides are homogeneous and stable and can be used successfully as adjuvants for herbicides.

These compositions are stable even at low temperature and can be used to prepare in locus diluted sprayable herbicidal formulations, in particular glyphosate formulations, without showing the crystallization problems found with other surfactants.

It is therefore an object of the present invention a homogeneous aqueous composition containing from about 10 to about 350 g/Kg of ammonium sulfate and from about 10 to about 200 g/Kg of anionic esters of linear or branched $C_6$-$C_{20}$ alkyl polyglycosides.

It is another object of the present invention a diluted sprayable herbicidal formulation comprising the above aqueous adjuvant compositions and at least a herbicide. The herbicide compositions can be employed in a method of treating crops with the herbicide compositions to reduce weeds.

DETAILED DESCRIPTION OF THE INVENTION

The homogeneous aqueous compositions of the invention comprise at least or about 30% by weight, preferably from about 40 to about 60% by weight, of water.

The anionic esters of alkylpolyglycosides utilisable for the realization of the present invention are compounds represented by the following formula (I) $[R—O—(G)_x]_n—(D)_y$, where R is an aliphatic alkyl group, saturated or unsaturated, linear or branched, having from 6 to 20 atoms of carbon, preferably from 8 to 12 carbon atoms; G is a residue of a reducing saccharide, preferably of glucose, connected to R—O by means of an ethereal O-glycosidical bond; O is an oxygen atom; D is an acyl residue connected to an oxygen atom of the residue G, and derived from a bicarboxylic acid or a polycarboxylic acid having an aliphatic chain from 2 to 8 carbon atoms, linear or branched, saturated or unsaturated, not substituted or substituted with one or more hydroxyl groups or a sulfonate group, and in which at least one carboxylic group is salified or in acid form; n is a number between 1 and m-1, where m is the number of carboxylic groups in the acid that originates D; x is a number from 1 to 10, representing the average degree of oligomerization of G; y is a number from 1 to 10 representing the medium degree of esterification. The above mentioned anionic esters of alkyl polyglycosides of formula (I) are known and they can be prepared as described, for example, in EP 258 814, EP 510 564 or EP 510 565.

In a preferred embodiment of this invention the concentration of ammonium sulfate in the composition is comprised between about 200 and about 340 g/Kg, the concentration of the anionic esters of alkyl polyglycosides is comprised between about 100 and about 200 g/kg and in formula (I) R is an aliphatic alkyl group, saturated or unsaturated, linear or branched, having from 8 to 12 carbon atoms;

more preferably in formula (I) D is the acyl residue of a carboxylic acid selected from the group consisting of citric acid, tartaric acid, maleic acid, malic acid and sulfosuccinic acid.

Anionic esters of alkyl polyglycosides of formula (I) in which R is an alkyl group having from 8 to 12 atoms of carbon and D is the acyl residue of sulfosuccinic acid (sulfosuccinic esters of $C_8$-$C_{12}$ alkyl polyglycosides) gave the best results in terms of the composition stability.

In the preferred embodiments, the anionic esters of alkyl polyglycosides are synthesized from alkyl polyglucosides with an alkyl group containing 8 to 12 carbon atoms and having an average degree of polymerization between 1.0 and 2.5.

Other nitrogenous fertilizers can be present in the composition of the invention.

Examples of suitable fertilizers are aqueous ammonia solutions, ammonium nitrate, ammonium hydrogen sulfate, ammonium chloride, ammonium acetate, ammonium formate, ammonium oxalate, ammonium carbonate, ammonium hydrogen carbonate, ammonium thiosulfate, ammonium phosphate, diammonium hydrogen phosphate, ammonium dihydrogen monophosphate, ammonium sodium hydrogen phosphate, ammonium thiocyanate, urea and thiourea, and mixtures of these, and also ammonium nitrate/urea solutions (UAN or AHL solutions).

Optionally, the homogeneous compositions also include drift retardants, humectants, corrosion inhibitors, microbial inhibitors, pH adjusters, anti-foam agents or mixture thereof.

The diluted sprayable herbicide formulations according to the invention are obtained by adding the homogeneous ammonium sulfate compositions to a formulated herbicide, or vice versa, and possibly diluting with water to the desired concentration in order to obtain aqueous formulation which can be directly sprayed on the fields.

Alternatively, the formulated herbicide and/or the homogeneous ammonium sulfate compositions may be previously diluted and then mixed. The term "diluted" is used herein with reference to herbicide active content comprised between 0.01 and 5% by weight.

Said sprayable herbicide formulations comprise herbicidal active compounds, such as Acetochlor, Alachlor, Atrazine, Bentazon, Bromacil, Chloridazon, Chlortoluron, Dalapon, Dicamba, Dichlorprop, Diuron, Ethofumesate, Fluometuron, Glufosinate, Glyphosate, Linuron, MCPA, MCPB, Metobromuron, Metolachlor, Oxadiazon, Paraquat, Pendimethalin, Phenmedipham, Propachlor, Propanil, -Propisochlor, Quizalofop-P-tefuryl, Sethoxydim, Simazine, Trifluralin, or mixtures thereof.

The adjuvant compositions of the present invention are particularly suited for the preparation of sprayable formulations of N-(phosphonomethyl) glycine (Glyphosate) and its salts, and preferably for the isopropylammonium salt of N-(phosphonomethyl) glycine (Glyphosate isopropylammonium).

Other biologically active ingredients such as other pesticides, plant growth regulators, algicides, fungicides, bactericides, viricides, insecticides, acaricides, nematicides and mixture thereof may be added as partners in the sprayable herbicide formulation.

The sprayable herbicidal formulations of the invention may additionally comprise other conventional additives, including thickeners, flow enhancers, wetting agents, buffers, lubricants, fillers, drift control agents, deposition enhancers, evaporation retardants, frost protecting agents, insect attracting odor agents, UV protecting agents, fragrances, anti-foam agents and mixtures thereof and the like.

Application rates will depend upon the weeds to be controlled and the degree of control desired. In general, the formulations of this invention are most efficiently employed at a rate of about 0.001 to about 22.4 kilograms per hectare of the active ingredients, preferably about 0.01 to 16.8 kilograms per hectare.

The homogeneous compositions of the invention are stable and can be stored for a long time without problem of crystallization of the ammonium sulfate.

Thanks to the presence of the anionic esters of alkyl polyglycosides, the ammonium sulfate does not precipitate out of the composition as such and even when other materials, such as the herbicide, are added to the composition.

The sprayable herbicidal formulations according to the invention have also high storage stability and do not tend to block the spray nozzles.

The following Examples serve to illustrate the stability of homogeneous compositions and of sprayable herbicide formulations according to the invention. A comparison is made with analogous compositions prepared from non ionic alkyl polyglycosides with the same alkyl chain length.

EXAMPLES

The following Examples describe the preparation of the ammonium sulfate (AMS) compositions.

Example 1 (Comparative)

340 g of AMS were dissolved in 490 g of water at 80° C. under stirring. After complete solubilization 170 g (dry matter) of a $C_{8-10}$ non ionic alkyl polyglucosides were added.

Example 2 (Comparative)

340 g of AMS were dissolved in 490 g of water at 80° C. under stirring. After complete solubilization 170 g (dry matter) of alkyl polyglucosides from $C_{10}$ linear alcohol and 2-ethyl hexanol were added.

Example 3

340 g of AMS were dissolved in 490 g of water at 80° C. under stirring. After complete solubilization 170 g (dry matter) of sulfosuccinic esters of $C_8$-$C_{10}$ alkyl polyglucosides were added.

Example 4

340 g of AMS were dissolved in 490 g of water at 80° C. under stirring. After complete solubilization 170 g (dry matter) of sulfosuccinic esters of an alkyl polyglucosides from $C_{10}$ linear alcohol and 2-ethyl hexanol were added.

Example 5

340 g of AMS were dissolved in 490 g of water at 80° C. under stirring. After complete solubilization 170 g (dry matter) of sulfosuccinic esters of isodecylic polyglucosides were added.

Example 6

340 g of AMS were dissolved in 490 g of water at 80° C. under stirring. After complete solubilization 170 g (dry matter) of sulfosuccinic esters of C9-C11 alkyl polyglucosides were added.

The results of the determination of the stability of the adjuvant compositions of Examples 1-6 are reported in Table 1.

TABLE 1

| Ammonium sulfate composition | APPEARANCE AT ROOM TEMP. | APPEARANCE AFTER 1 WEEK AT 4° C. | APPEARANCE AFTER 2 WEEK AT 4° C. |
|---|---|---|---|
| Example 1* | NO CRYSTALS | SOME CRYSTALS | CRYSTALS |
| Example 2* | NO CRYSTALS | NO CRYSTALS | CRYSTALS |
| Example 3 | NO CRYSTALS | NO CRYSTALS | NO CRYSTALS |

TABLE 1-continued

| Ammonium sulfate composition | APPEARANCE AT ROOM TEMP. | APPEARANCE AFTER 1 WEEK AT 4° C. | APPEARANCE AFTER 2 WEEK AT 4° C. |
|---|---|---|---|
| Example 4 | NO CRYSTALS | NO CRYSTALS | NO CRYSTALS |
| Example 5 | NO CRYSTALS | NO CRYSTALS | NO CRYSTALS |
| Example 6 | NO CRYSTALS | NO CRYSTALS | NO CRYSTALS |

*comparative

The following Examples describe the preparation of sprayable herbicide formulations.

Example 7

1 g of a commercial formulation of glyphosate, containing 360 g/l of isopropylammonium glyphosate salt, and 0.6 g of the ammonium sulfate composition of Example 3 were mixed with 98.4 g of Cipac D standard water (CIPAC MT 18) at room temperature under stirring.

Example 8

1 g of a commercial formulation of glyphosate, containing 360 g/l of isopropylammonium glyphosate salt, and 1.2 g of the ammonium sulfate composition of Example 3 were mixed with 97.8 g of Cipac D standard water (CIPAC MT 18) at room temperature under stirring.

Example 9

1 g of a commercial formulation of glyphosate, containing 360 g/l of isopropylammonium glyphosate salt, and 0.6 g of the ammonium sulfate composition of Example 5 were mixed with 98.4 g of Cipac D standard water (CIPAC MT 18) at room temperature under stirring.

Example 10

1 g of a commercial formulation of glyphosate, containing 360 g/l of isopropylammonium glyphosate salt, and 1.2 g of the ammonium sulfate composition of Example 5 were mixed with 97.8 g of Cipac D standard water (CIPAC MT 18) at room temperature under stirring.

The results of the determination of the stability of the sprayable herbicide formulations of Examples 8-11 are reported in Table 2.

TABLE 2

| SPRAYABLE HERBICIDE FORMULATION | APPEARANCE AFTER 24 h AT ROOM TEMPERATURE | APPEARANCE AFTER 24 h AT 4° C. |
|---|---|---|
| Example 7 | NO CRYSTALS | NO CRYSTALS |
| Example 8 | NO CRYSTALS | NO CRYSTALS |
| Example 9 | NO CRYSTALS | NO CRYSTALS |
| Example 10 | NO CRYSTALS | NO CRYSTALS |

The invention claimed is:

1. A stable homogeneous aqueous composition comprising from 200 to 350 g/Kg of ammonium sulfate and from about 100 to about 200 g/Kg of anionic esters of linear or branched $C_6$-$C_{12}$ alkyl polyglucoside; wherein the anionic esters of alkyl polyglycosides are compounds represented by the formula:

$$[R\text{—}O\text{-}(G)_x]_n\text{-}(D)_y \quad (I)$$

where:
R is an aliphatic alkyl group, saturated or unsaturated, linear or branched, having from 6 to 12 atoms of carbon;
G is a residue of glucose, connected to R—O by means of an ethereal O-glycosidical bond;
O is an oxygen atom;
D is an acyl residue D is the acyl residue of sulfosuccinic acid, and in which at least one carboxylic group is salified or in acid form;
n is a number between 1 and m-1, where m is the number of carboxylic groups in the acid that originates D;
x is a number from 1 to 10, representing the average degree of oligomerization of G;
y is a number from 1 to 10 representing the medium degree of esterification.

2. The homogeneous aqueous composition of claim 1 wherein the ammonium sulfate is present at a concentration of from about 200 to about 340 g/kg and the anionic ester of formula (I) is present at a concentration of from about 100 to about 200 g/kg.

3. The homogeneous aqueous composition of claim 1 wherein the concentration of water present in the homogeneous aqueous composition is from about 30 to about 60 percent by weight.

4. The homogeneous aqueous composition of claim 3 wherein the concentration of water present in the homogeneous aqueous composition is from about 40 to about 60 percent by weight.

5. A sprayable herbicidal formulation comprising the aqueous composition of claim 1 and from 0.01 to 5% by weight of at least one herbicide.

6. The sprayable herbicidal formulation of claim 5 wherein the at least one herbicide comprises an herbicidal active compound selected from the group consisting of Acetochlor, Alachlor, Atrazine, Bentozon, Bromacil, Chloridazon, Chlortoluron, Dalapon, Dicamba, Dichlorprop, Diuron, Ethofumesate, Fluometuron, Glufosinate, Glyphosate, Linuron, MCPA, MCPB, Metobromuron, Metolachlor, Oxadiazon, Paraquat, Pendimethalin, 10 Phenmedipham, Propachlor, Propanil, - Propisochlor, Quizalofop-P-tefuryl, Sethoxydim, Simazine, Trifluralin, and mixtures thereof.

7. The sprayable herbicidal formulation of claim 5 wherein the herbicide is N-(phosphonomethyl) glycine (Glyphosate) and its salts.

8. The sprayable herbicidal formulation of claim 5 wherein the herbicide is the isopropylammonium salt of N-(phosphonomethyl) glycine (Glyphosate isopropylammonium).

9. The sprayable herbicidal formulation of claim 5 additionally comprising a composition selected from the group consisting of pesticides, plant growth regulators, algicides, fungicides, bactericides, viricides, insecticides, acaricides, nematicides, and mixtures thereof.

10. The sprayable herbicidal formulation of claim 9 additionally comprising a composition selected from the group consisting of thickeners, flow enhancers, wetting agents, buffers, lubricants, fillers, drift control agents, deposition enhancers, evaporation retardants, frost protecting agents, 25 insect attracting odor agents, UV protecting agents, fragrances, anti-foam agents, and mixtures thereof.

11. The sprayable herbicidal formulation of claim 5 additionally comprising a nitrogenous fertilizer other than ammonium sulfate.

12. The sprayable herbicidal formulation of claim 11 wherein the nitrogenous fertilizer other than ammonium sulfate is selected from the group consisting of aqueous ammonium solutions, ammonium nitrate, ammonium hydrogen sulfate, ammonium chloride, ammonium acetate, ammonium formate, ammonium oxalate, ammonium carbonate, ammonium hydrogen carbonate, ammonium thiosulfate, ammonium phosphate, diammonium hydrogen phosphate, ammonium dihydrogen monophosphate, ammonium sodium hydrogen phosphate, ammonium thiocyanate, urea, thiourea, and mixtures thereof.

13. A method for treating crops to reduce weeds comprising applying the homogeneous aqueous composition of claim 1 to the crops.

14. The method of claim 13 wherein the homogeneous aqueous composition is applied at a rate of from about 0.001 to 22.4 kg of active ingredients per hectare.

15. The method of claim 14 wherein the homogeneous aqueous composition is applied at a rate of from about 0.01 to 16.8 kg of active ingredients per hectare.

* * * * *